United States Patent
Amorelli et al.

(10) Patent No.: US 11,091,418 B2
(45) Date of Patent: Aug. 17, 2021

(54) ORGANOLEPTIC COMPOUNDS

(71) Applicant: International Flavors & Fragrances Inc., New York, NY (US)

(72) Inventors: Benjamin Amorelli, Brielle, NJ (US); Robert P. Belko, Monroe, NJ (US); Anthony T. Levorse, Jr., Westfield, NJ (US); Michael G. Monteleone, Hazlet, NJ (US); Richard Payne, Brielle, NJ (US); Iyare Amegor, Newark, NJ (US); Feng Geng, Piscataway, NJ (US); David Rodriguez, Belleville, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

(21) Appl. No.: 15/998,616

(22) PCT Filed: Feb. 17, 2017

(86) PCT No.: PCT/US2017/018366
§ 371 (c)(1),
(2) Date: Aug. 16, 2018

(87) PCT Pub. No.: WO2017/143187
PCT Pub. Date: Aug. 24, 2017

(65) Prior Publication Data
US 2020/0331834 A1    Oct. 22, 2020

Related U.S. Application Data

(60) Provisional application No. 62/296,370, filed on Feb. 17, 2016.

(51) Int. Cl.
C07C 47/115    (2006.01)
C07C 47/225    (2006.01)
C11D 3/50      (2006.01)

(52) U.S. Cl.
CPC .......... *C07C 47/115* (2013.01); *C07C 47/225* (2013.01); *C11D 3/50* (2013.01)

(58) Field of Classification Search
CPC ....................................................... C11D 3/50
See application file for complete search history.

(56) References Cited

U.S. PATENT DOCUMENTS

| 8,309,511 B1 | 11/2012 | Weiss et al. |
| 2009/0131299 A1 | 5/2009 | Dilk et al. |
| 2014/0107220 A1* | 4/2014 | Narula .................. C07C 47/347 514/693 |
| 2015/0374599 A1 | 12/2015 | Schmaus et al. |

FOREIGN PATENT DOCUMENTS

KR    20150070937 A    6/2015

OTHER PUBLICATIONS

International Preliminary Report on Patentability in PCT/US2017/018366 dated Aug. 21, 2018.
International Search Report and Written Opinion in PCT/US2017/018366 dated May 29, 2017.
Extended European Search Report dated Sep. 16, 2019 for EP 17753924.4 filed Feb. 17, 2017.
Brunke et al. (1995) "Cyclosantalal and epicyclosantalal—new sesquiterpene aldehydes from east Indian sandalwood oil," Flavor and Fragrance Journal 10(3):211-219.

* cited by examiner

*Primary Examiner* — Arrie L Reuther
(74) *Attorney, Agent, or Firm* — Licata & Tyrrell P.C.

(57) ABSTRACT

The present invention relates to novel compounds and their use as fragrance materials.

18 Claims, No Drawings

ORGANOLEPTIC COMPOUNDS

STATUS OF RELATED APPLICATIONS

This application claims priority to U.S. provisional application 62/296,370 filed Feb. 17, 2016, the content hereby incorporated by reference as if set forth in its entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel compounds and their unexpected advantageous use in enhancing, improving or modifying the fragrance of perfumes, colognes, toilet water, fabric care products, personal products and the like.

More specifically, an embodiment of the present invention relates to novel 4,7-methano-indene derivatives represented by Formula I including Formulas Ia and Ib, Formula II including Formulas IIa and IIb, Formula III including Formulas Ma and Mb, and Formula IV including Formulas IVa and IVb which exhibit unexpected woody, floral, muguet, green, aldehydic and slight orris notes, and a method of improving, enhancing or modifying a fragrance formulation through the addition of an olfactory acceptable amount of these 4,7-methano-indene derivatives.

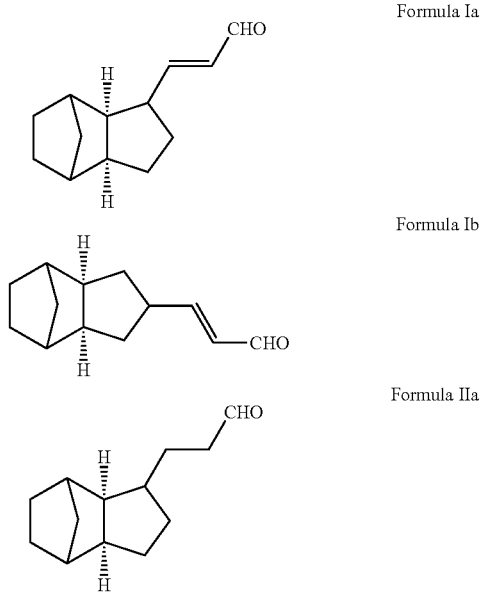

Formula Ia

Formula Ib

Formula IIa

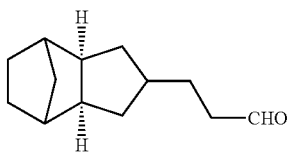

Formula IIb

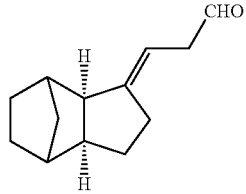

Formula IIIa

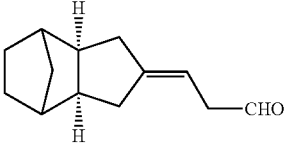

Formula IIIb

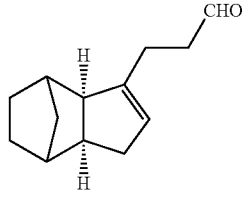

Formula IVa

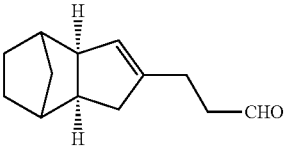

Formula IVb wherein Formula Ia represents (3aS,7aR)-3-(octahydro-4,7-methano-inden-1-yl)-propenal (rel); Formula Ib represents (3aS,7aR)-3-(octahydro-4,7-methano-inden-2-yl)-propenal (rel); Formula Ha represents (3aS,7aR)-3-(octahydro-4,7-methano-inden-1-yl)-propionaldehyde (rel); Formula IIb represents (3aS,7aR)-3-(octahydro-4,7-methano-inden-2-yl)-propionaldehyde (rel); Formula Ma represents (3aS,7aR)-3[octahydro-4,7-methano-inden-(1E)-ylidene]-propionaldehyde (rel); Formula IIIb represents (3aS,7aR)-3[octahydro-4,7-methano-inden-(2E)-ylidene]-propionaldehyde (rel); Formula IVa represents (3 aS,7aR)-3-(3 a,4,5, 6,7,7a-hexahydro-3H-4,7-methano-inden-1-yl)-propionaldehyde (rel); and Formula IVb represents (3aR,7aS)-3-(3a,4,5,6,7,7a-hexahydro-1H-4,7-methano-inden-2-yl)-propionaldehyde (rel). Formula I refers to the mixture of Formula la and Ib; Formula II refers to the mixture of Formula Ha and Hb; Formula III refers to the mixture of Formula Ma and IIIb; and Formula IV refers to the mixture of Formula IVa and IVb.

More specifically, the present invention is directed to novel 4,7-methano-indenes of:
(i) (3aS,7aR)-3-(octahydro-4,7-methano-inden-1-yl)-prop enal (rel), (3aS,7aR)-3-(octahydro-4,7-methano-inden-2-yl)-propenal (rel), and a mixture thereof;
(ii) (3aS,7aR)-3-(octahydro-4,7-methano-inden-1-yl)-propionaldehyde (rel), (3aS,7aR)-3-(octahydro-4,7-methano-inden-2-yl)-propionaldehyde (rel), and a mixture thereof;

(iii) (3aS,7aR)-3-[octahydro-4,7-methano-inden-(1E)-ylidene]-prop ionaldehyde (rel), (3aS,7aR)-3-[octahydro-4,7-methano-inden-(2E)-ylidene]-propionaldehyde (rel), and a mixture thereof; and
(iv) (3aS,7aR)-3-(3a,4,5,6,7,7a-hexahydro-3H-4,7-methano-inden-1-yl)-propionaldehyde (rel), (3aR,7aS)-3-(3a,4,5,6,7,7a-hexahydro-1H-4,7-methano-inden-2-yl)-propionaldehyde (rel), and a mixture thereof.

Another embodiment of the present invention relates to a novel compound 2-13,3-dimethyl-cyclohexylidenel-propionitrile represented by Formula V, which exhibits unexpected tobacco, hay, herbal, spicy, wood and fruity notes, and a method of improving, enhancing or modifying a fragrance formulation through the addition of an olfactory acceptable amount of this compound.

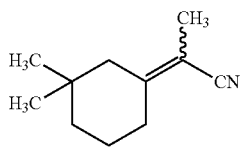

Formula V

Another embodiment of the present invention relates to a fragrance composition comprising the novel compounds provided above.

Another embodiment of the present invention relates to a fragrance product comprising the compounds provided above.

Another embodiment of the present invention relates to a method of improving, enhancing or modifying a fragrance formulation through the addition of an olfactory acceptable amount of the novel compounds provided above.

These and other embodiments of the present invention will be apparent by reading the following specification.

DETAILED DESCRIPTION OF THE INVENTION

It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly silica gel chromatography and gas chromatography trapping known as GC trapping. Yet, commercial products are mostly offered as isomeric mixtures.

The preparation of the compounds of the present invention is detailed in the Examples. Materials were purchased from Aldrich Chemical Company unless noted otherwise.

The use of the compounds of the present invention is widely applicable in current perfumery products, including the preparation of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in Perfumes, Cosmetics and Soaps, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with an additional fragrance compound. The term "additional fragrance compound" as used herein is defined as a fragrance compound selected from the group consisting of 2-[(4-methylphenyl)methylenel]-heptanal (Acalea), decanal (Aldehyde C-10), 2-methyl undecanal (Aldehyde C-12 MNA), iso-amyl oxyacetic acid allylester (Allyl Amyl Glycolate), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylb icyclo [2.2.1]hept-2-yDoxy] exo-1-propanol (Bornafix), 1,2,3,5,6,7-hexahydro-1, 1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1G-inden-5/6-yl propinoate (Cyclaprop), 3A,4,5,6,7,7A-hexahydro-4,7-methano-1G-inden-5/6-yl butyrate (Cyclobutanate), 4-(2,6,6-trimethyl-cyclohexen-2-yl)-2-buten-4-one (Alpha Damascone), 1-(2,6,6-trimethyl-3-cyclohexen-1-yl))-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclop enta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexalon), 3-hexen-1-ol, (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8,8A-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methyl-pentyl) cyclohexene-1-carboxaldehyde (Lyral), 3-methyl-4-(2,6,6-trimethyl-2-cyclohexen-1-yl)-3-buten-2-one (Methyl Ionone y), 1-(2,6,6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl) cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-prop enyl)oxy]-3-hexene (Vivaldie).

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention comprises a compound of the present invention and further a complementary fragrance compound. The term "complementary fragrance compound" as used herein is defined as a fragrance compound selected from the group consisting of decanal, 2-methyl undecanal; 3-hexen-1-ol, 4-(2,6,6-trimethyl-2-cyclohexen-1-yl)-3-buten-2-one; 3-methyl-4-(2,6,6-trimethyl-2-cyclohexen-1-yl)-3-buten-2-one; 1-(2,6,6-trimethyl-2-cyclohexen-1-yl)pent-1-en-3-one; methyl 3-oxo-2-pentylcyclop entaneacetate; 2,4-dimethyl-3-cyclohexene-1-carboxaldehyde; 2-tert-butylcyclohexyl acetate; 4-(2,6,6-trimethyl-cyclohexen-2-yl)-2-buten-4-one, 1-(2,6,6-trimethyl-3-cyclohexen-1-yl)-2-buten-1-one; 1-(1,2,3,4,5,6,7,8,8A-octahydro-2,3,8,8-tetramethyl-2-naphthalenyl)-ethan-1-one; and a mixture thereof.

The term "fragrance product" means a consumer product containing a fragrance ingredient that adds fragrance or masks malodor. Fragrance products may include, for example, perfumes, colognes, bar soaps, liquid soaps, shower gels, foam baths, cosmetics, skin care products such as creams, lotions and shaving products, hair care products for shampooing, rinsing, conditioning, bleaching, coloring, dyeing and styling, deodorants and antiperspirants, feminine care products such as tampons and feminine napkins, baby care products such as diapers, bibs and wipes, family care products such as bath tissues, facial tissues, paper handkerchiefs or paper towels, fabric products such as fabric softeners and fresheners, air care products such as air fresheners and fragrance delivery systems, cosmetic preparations, cleaning agents and disinfectants such as detergents, dishwashing materials, scrubbing compositions, glass and metal cleaners such as window cleaners, countertop cleaners, floor and carpet cleaners, toilet cleaners and bleach additives, washing agents such as all-purpose, heavy duty, and hand washing or fine fabric washing agents including laundry detergents and rinse additives, dental and oral hygiene products such as toothpastes, tooth gels, dental flosses, denture cleansers, denture adhesives, dentifrices, tooth whitening and mouthwashes, health care and nutritional products and food products such as snack and beverage products. The fragrance product of the present invention is a consumer product that contains a compound of the present invention. The fragrance product of the present invention contains a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

The term "olfactory acceptable amount" is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compound of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation to encapsulate and/or deliver the fragrance. Some well-known materials are, for example, but not limited to, polymers, oligomers, other non-polymers such as surfactants, emulsifiers, lipids including fats, waxes and phospholipids, organic oils, mineral oils, petrolatum, natural oils, perfume fixatives, fibers, starches, sugars and solid surface materials such as zeolite and silica.

When used in a fragrance formulation these ingredients provide additional notes to make a fragrance formulation more desirable and noticeable, and add the perception of value. The odor qualities found in these materials assist in beautifying and enhancing the finished accord as well as improving the performance of the other materials in the fragrance.

In addition, the compounds of the present invention are also surprisingly found to provide superior ingredient performance and possess unexpected advantages in malodor counteracting applications such as body perspiration, environmental odor such as mold and mildew, bathroom, and etc. The compounds of the present invention substantially eliminate the perception of malodors and/or prevent the formation of such malodors, thus, can be utilized with a vast number of functional products.

Examples of the functional products are provided herein to illustrate the various aspects of the present invention. However, they do not intend to limit the scope of the present invention. The functional products may include, for example, a conventional room freshener (or deodorant) composition such as room freshener sprays, an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towellets, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processings, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, and subways and transport systems.

Thus, it will be seen that the composition of the invention is usually one in which the malodor counteractant is present together with a carrier by means of which or from which the malodor counteractant can be introduced into air space wherein the malodor is present, or a substrate on which the malodor has deposited. For example, the carrier can be an aerosol propellant such as a chlorofluoro-methane, or a solid such as a wax, plastics material, rubber, inert powder or gel. In a wick-type air freshener, the carrier is a substantially odorless liquid of low volatility. In several applications, a composition of the invention contains a surface active agent or a disinfectant, while in others, the malodor counteractant is present on a fibrous substrate. In many compositions of the invention there is also present a fragrance component which imparts a fragrance to the composition. The fragrances stated above can all be employed.

Malodor counteracting effective amount is understood to mean the amount of the inventive malodor counteractant employed in a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteractancy desired. In general, the amount of malodor counteractant agent present is the ordinary dosage required to obtain the desired result. Such dosage is known to the skilled practitioner in the art. In a preferred embodiment, when used in conjunction with malodorous solid or liquid functional products, e.g., soap and detergent, the compounds of the present invention may be present in an amount ranging from about 0.005 to about 50 weight percent, preferably from about 0.01 to about 20 weight percent, and more preferably from about 0.05 to about 5 weight percent, and when used in conjunction with malodorous gaseous functional products, the compounds of the present invention may be present in an amount ranging from about 0.1 to 10 mg per cubic meter of air.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, Kg is understood to be kilogram, mol is understood to be mole, psi is understood to be pound-force per square inch, and mmHg be millimeters (mm) of mercury (Hg). IFF as used in the examples is understood to mean International Flavors & Fragrances Inc., New York, N.Y., USA.

EXAMPLE I

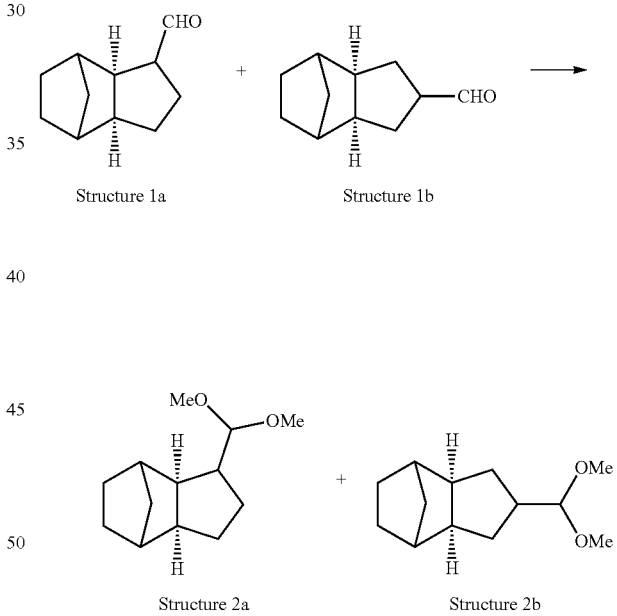

Preparation of (3aS,7aR)-1-Dimethoxymethyl-octahydro-4,7-methano-indene (rel) (Structure 2a) and (3aS,7aR)-2-Dimethoxymethyl-octahydro-4,7-methano-indene (rel) (Structure 2b): A mixture of (3aS,7aR)-octahydro-4,7-methano-indene-1-carbaldehyde (rel) (Structure 1a)/(3aS,7aR)-octahydro-4,7-methano-indene-2-carbaldehyde (rel) (Structure 1b) (1Kg, 6.09 mol), trimethylorthoformate (CH(OCH$_3$)$_3$) (969 g, 9.13 mol) and methanol (CH$_3$OH) (500 mL) was cooled to −15° C. Hydrochloric acid (HCl) (37%, 2 mL) was then added and allowed to exotherm. The reaction mixture was warmed to room temperature, aged while stirring for additional 2 hours and then quenched with sodium methoxide (CH$_3$ONa) in methanol (25%, 20 g). The resulting mixture was distilled (101° C., 1 torr) to provide a mixture of (3aS,7aR)-1-dimethoxymethyl-octahydro-4,7-methano-indene (rel) (Structure 2a) and (3aS,7aR)-2-dimethoxymethyl-octahydro-4,7-methano-indene (rel) (Structure 2b) (1.181 Kg).

The mixture obtained in the above preparation possessed the NMR spectral characteristics of: $^1$H NMR (500 MHz, CDCl$_3$): 4.13 ppm (d, 1H, J=6.9 Hz), 3.36 ppm (s, 3H), 3.32 ppm (s, 3H), 2.07-2.12 ppm (m, 1H), 0.90-1.95 ppm (m, 14H)

EXAMPLE II

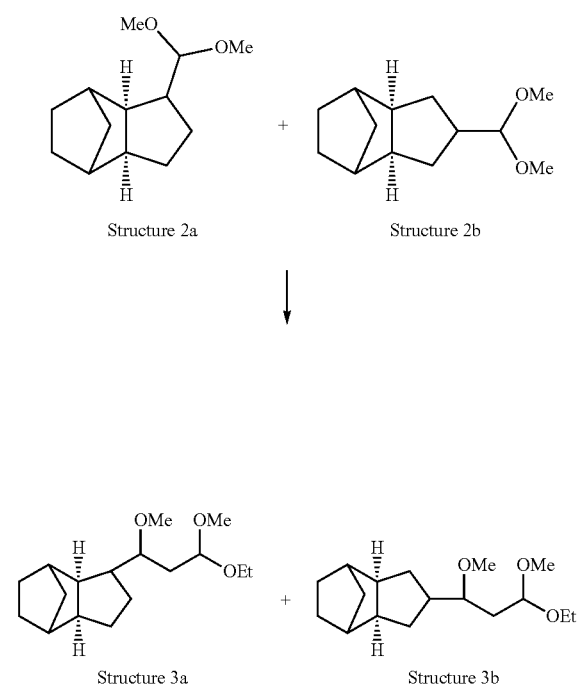

Structure 2a  Structure 2b

Preparation of (3aS,7aR)-1-(3-Ethoxy-1,3-dimethoxy-propyl)-octahydro-4,7-methano-indene (rel) (Structure 3a) and (3aS,7aR)-2-(3-ethoxy-1,3-dimethoxy-propyl)-octahydro-4,7-methano-indene (rel) (Structure 3b): Boron trifluoride etherate (BF$_3$.O(C$_2$H$_5$)$_2$) (2 g) was added to the mixture of (3aS,7aR)-1-dimethoxymethyl-octahydro-4,7-methano-indene (rel) (Structure 2a) and (3aS,7aR)-2-dimethoxymethyl-octahydro-4,7-methano-indene (rel) (Structure 2b) (1.782 Kg, 8.47 mol) (obtained as above in EXAMPLE I) at about 32° C. Ethyl vinyl ether (C$_2$H$_5$OCHCH$_2$) (792 g, 11.0 mol) was added dropwise over a 2 hour period. The reaction mixture was quenched with solid sodium acetate (CH$_3$COONa) (10 g) followed by aqueous sodium carbonate (Na$_2$CO$_3$) (10%) and aged for 30 minutes. The organic layer was separated, dried over sodium sulfate (Na$_2$SO$_4$), filtered and then distilled (139° C., 1 torr) to afford a crude mixture of (3aS,7aR)-1-(3-ethoxy-1,3-dimethoxy-propyl)-octahydro-4,7-methano-indene (rel) (Structure 3a) and (3aS, 7aR)-2-(3-ethoxy-1,3-dimethoxy-propyl)-octahydro-4,7-methano-indene (rel) (Structure 3b) (1.266 Kg). The obtained crude mixture was used directly in the following steps.

The mixture obtained in the above preparation possessed the NMR spectral characteristics of: $^1$H NMR (500 MHz, CDCl$_3$): 4.50-4.52 ppm (m, 1H), 3.49-3.52 ppm (m, 2H), 3.48 ppm (s, 3H), 3.46 (s, 3H), 3.20-3.40 ppm (m, 1H), 0.90-2.10 ppm (m, 20H)

EXAMPLE III

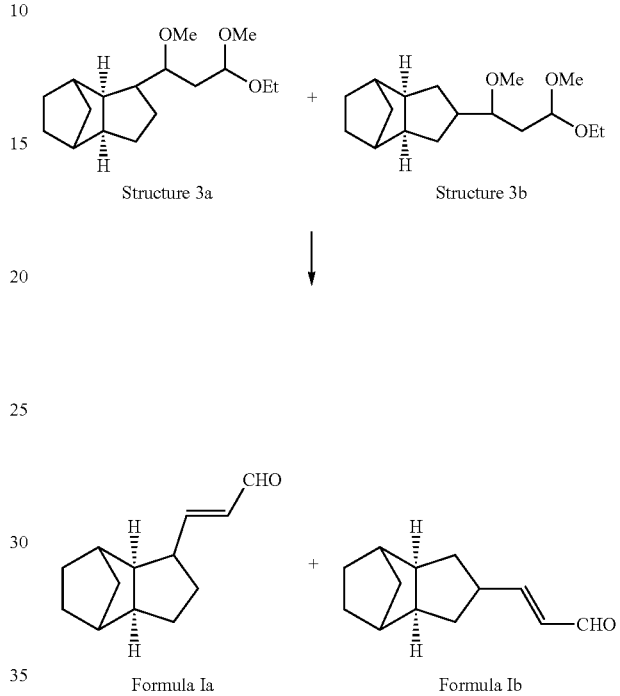

Structure 3a  Structure 3b

Formula Ia  Formula Ib

Preparation of (3aS,7aR)-3-(Octahydro-4,7-methano-inden-1-yl)-propenal (rel) (Formula Ia) and (3aS,7aR)-3-(octahydro-4,7-methano-inden-2-yl)-propenal (rel) (Formula Ib): Hydrochloric acid (37%, 50 g) was added to the crude mixture of (3aS,7aR)-1-(3-ethoxy-1,3-dimethoxy-propyl)-octahydro-4,7-methano-indene (rel) (Structure 3a) and (3aS, 7aR)-2-(3-ethoxy-1,3-dimethoxy-propyl)-octahydro-4,7-methano-indene (rel) (Structure 3b) (obtained as above in EXAMPLE II) (1.266 Kg) in water (500 mL) while stirring. The reaction mixture was refluxed while low boiling alcohol(s) was distilled off up to a temperature of about 115° C. The resulting mixture was allowed to cool to room temperature. The organic layer was separated, washed with sodium bicarbonate until neutral, dried over sodium sulfate, filtered and distilled (118° C., 1.5 torr) to provide Formula I of the mixture of (3aS,7aR)-3-(octahydro-4,7-methano-inden-1-yl)-prop enal (rel) (Formula Ia) and (3 aS,7aR)-3-(octahydro-4,7-methano-inden-2-yl)-propenal (rel) (Formula Ib) with a weight ratio Formulas Ia:Ib at 3:1 (703 g). (3aS,7aR)-3-(Octahydro-4,7-methano-inden-1-yl)-propenal (rel) (Formula Ia) possessed the NMR spectral characteristics of:

$^1$H NMR (500 MHz, CDCl$_3$): 9.51 (d, J=8.2 Hz, 1H), 6.84 (dd, J=15.5, 7.8 Hz, 1H), 6.10 (ddd, J=15.5, 7.8, 1.3 Hz, 1H), 0.82-2.25 (m, 17H)

(3aS,7aR)-3-(Octahydro-4,7-methano-inden-2-yl)-propenal (rel) (Formula Ib) possessed the NMR spectral characteristics of:

$^1$H NMR (500 MHz, CDCl$_3$): 9.47 (d, J=7.9 Hz, 1H), 6.74 (dd, J=15.5, 7.8 Hz, 1H), 6.06 (ddd, J=15.5, 7.8, 1.3 Hz, 1H), 0.82-2.25 (m, 17H)

Formula I was described as having woody, floral, muguet, green, aldehydic and orris notes.

EXAMPLE IV

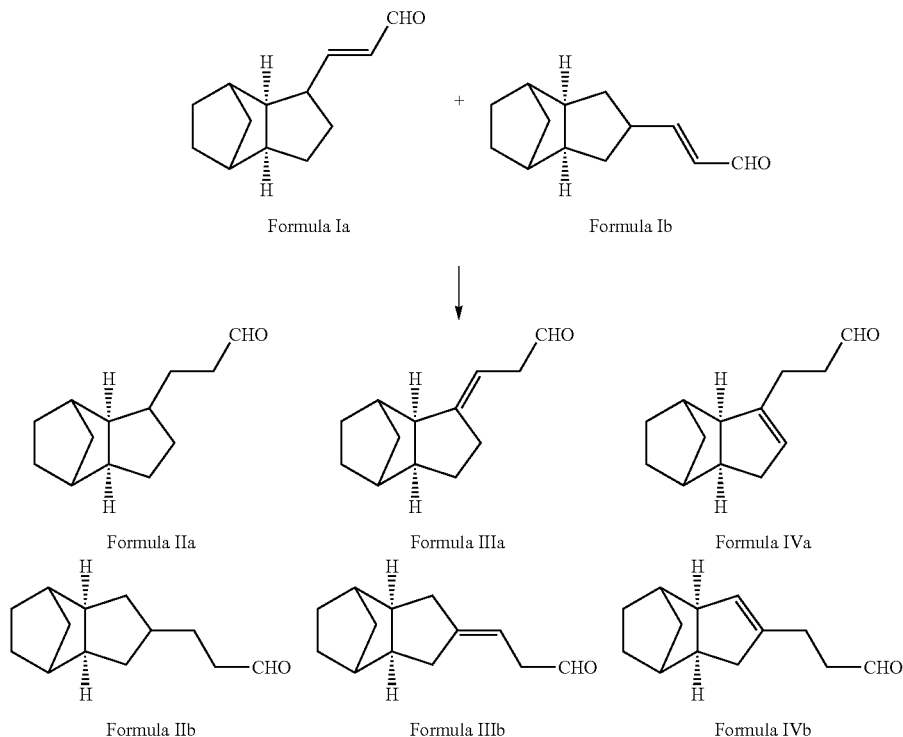

Preparation of (3aS,7aR)-3-(Octahydro-4,7-methano-inden-1-yl)-propionaldehyde (rel) (Formula IIa), (3aS,7aR)-3-(Octahydro-4,7-methano-inden-2-yl)-propionaldehyde (rel) (Formula IIb), (3aS,7aR)-3-10ctahydro-4,7-methano-inden-(1E)-ylidenej-propionaldehyde (rel) (Formula IIIa), (3aS,7aR)-3-10ctahydro-4,7-methano-inden-(2E)-ylidenej-propionaldehyde (rel) (Formula IIIb), (3aS,7aR)-3-(3a,4,5,6,7,7a-Hexahydro-3H-4,7-methano-inden-1-yl)-propionaldehyde (rel) (Formula IVa) and (3aR,7aS)-3-(3a,4,5,6,7,7a-Hexahydro-1H-4,7-methano-inden-2-yl)-propionaldehyde (rel) (Formula IVb): The crude product of Formula I (obtained as above in EXAMPLE III) (703 g) and isopropanol ((CH$_3$)$_2$CHOH) (20 mL) were hydrogenated with palladium on carbon (Pd/C) (5%, 3 g) under 200 psi of hydrogen at 75° C. for 4 hours. The resulting mixture was filtered through celite, washed with hot water (500 mL for twice) and then distilled (108° C., 2.3 torr) to provide a mixture of Formula II of (3aS,7aR)-3-(octahydro-4,7-methano-inden-1-yl)-propionaldehyde (rel) (Formula IIa) and (3aS,7aR)-3-(octahydro-4,7-methano-inden-2-yl)-propionaldehyde (rel) (Formula IIb), Formula III of (3aS,7aR)-3-[octahydro-4,7-methano-inden-(1E)-ylidene]-propionaldehyde (rel) (Formula IIIa) and (3aS,7aR)-3-[octahydro-4,7-methano-inden-(2E)-ylidene]-propionaldehyde (rel) (Formula IIIb), and Formula IV of (3aS,7aR)-3-(3a,4,5,6,7,7a-hexahydro-3H-4,7-methano-inden-1-yl)-propionaldehyde (rel) (Formula IVa) and (3aR,7aS)-3-(3a,4,5,6,7,7a-hexahydro-1H-4,7-methano-inden-2-yl)-propionaldehyde (rel) (Formula IVb) with a weight ratio of Formulas II:III:IV at 64:1:2 (610 g).

(3aS,7aR)-3-(Octahydro-4,7-methano-inden-1-yl)-propionaldehyde (rel) (Formula IIa) possessed the NMR spectral characteristics of:
$^1$H NMR (500 MHz, CDCl$_3$): 9.77 ppm (t, 1H, J=1.80 Hz), 2.47 ppm (t, 2H, J=7.25 Hz), 0.85-1.98 ppm (m, 17H)

(3aS,7aR)-3-(Octahydro-4,7-methano-inden-2-yl)-propionaldehyde (rel) (Formula IIb) possessed the NMR spectral characteristics of:
$^1$H NMR (500 MHz, CDCl$_3$): 9.76 ppm (t, 1H, J=1.8 Hz), 2.34-2.44 ppm (m, 2H), 0.85-1.98 ppm (m, 17H)

(3aS,7aR)-3-[Octahydro-4,7-methano-inden-(1E)-ylidene]-propionaldehyde (rel) (Formula IIIa) possessed the NMR spectral characteristics of:
$^1$H NMR (400 MHz, CDCl$_3$): 9.62 (t, J=2.1 Hz, 1H), 5.31-5.42 (m, 1H), 3.03-3.25 (m, 2H), 0.83-2.60 (m, 14H)

(3aS,7aR)-3-[Octahydro-4,7-methano-inden-(2E)-ylidene]-propionaldehyde (rel) (Formula IIIb) possessed the NMR spectral characteristics of:
$^1$H NMR (400 MHz, CDCl$_3$): 9.61 (t, J=2.1 Hz, 1H), 5.21-5.29 (m, 1H), 3.03-3.25 (m, 2H), 0.83-2.60 (m, 14H)

(3aS,7aR)-3-(3a,4,5,6,7,7a-Hexahydro-3H-4,7-methano-inden-1-yl)-propionaldehyde (rel) (Formula IVa) possessed the NMR spectral characteristics of:
$^1$H NMR (400 MHz, CDCl$_3$): 9.74-9.81 (m, 1H), 5.23-5.30 (m, 1H), 0.67-2.69 (m, 16H)

(3aR,7aS)-3-(3a,4,5,6,7,7a-Hexahydro-1H-4,7-methano-inden-2-yl)-propionaldehyde (rel) (Formula IVb) possessed the NMR spectral characteristics of:
$^1$H NMR (400 MHz, CDCl$_3$): 9.74-9.81 (m, 1H), 5.10-5.16 (m, 1H), 0.67-2.69 (m, 16H)

Formula II was described as having muguet, melon-like, green, ozonic, aldehydic and cuminic notes.

Formula IV was described as having melon-like, green, cucumber-like and aldehydic notes.

The mixture of Formula II, Formula III and Formula IV was described as having floral, muguet, green, aldehydic and slight orris notes.

EXAMPLE V

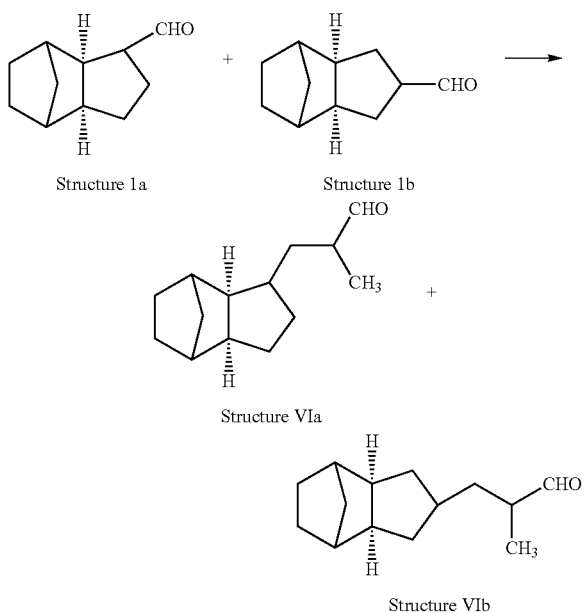

Structure Ia    Structure Ib

Structure VIa

Structure VIb

Preparation of 2-Methyl-(3aS,7aR)-3-(octahydro-4,7-methano-inden-1-yl)-propionaldehyde (rel) (Formula VIa) and 2-Methyl-(3aS,7aR)-3-(Octahydro-4,7-methano-inden-2-yl)-propionaldehyde (rel) (Formula VIb): A mixture of (3aS,7aR)-octahydro-4,7-methano-indene-1-carbaldehyde (rel) (Structure 1a)/(3aS,7aR)-octahydro-4,7-methano-indene-2-carbaldehyde (rel) (Structure 1b) (1.15 Kg, 7 mol), potassium hydroxide (KOH) (50 g, 0.9 mol) and methanol (CH$_3$OH) (500 mL) were combined at 25° C. Propionaldehyde (580 g, 10 mol) was added dropwise over a 4 hour period while the temperature was maintained at 25-30° C. The reaction was aged for additional 1 hour. Acetic acid (CH$_3$COOH) (100 g) was added and the solvent was removed via distillation to an internal temperature of 90° C. The reaction mass was then cooled and washed with water (500 mL for twice). The resulting mixture was hydrogenated with palladium on carbon (5%, 10 g) under 100 psi of hydrogen at 100° C. The crude was then distilled to provide Formula VI of the mixture of 2-methyl-(3aS,7aR)-3-(octahydro-4,7-methano-inden-1-yl)-propionaldehyde (rel) (Formula VIa) and 2-methyl-(3aS,7aR)-3-(Octahydro-4,7-methano-inden-2-yl)-propionaldehyde (rel) (Formula VIb) (1.1 kg).

2-Methyl-(3aS,7aR)-3-(octahydro-4,7-methano-inden-1-yl)-propionaldehyde (rel) (Formula VIa) possessed the NMR spectral characteristics of:

$^1$FINMR (400 MHz, CDCl$_3$): 9.61 (t, J=2.3 Hz, 1H), 0.52-2.58 (m, 21H) 2-Methyl-(3aS,7aR)-3-(Octahydro-4,7-methano-inden-2-yl)-propionaldehyde (rel) (Formula VIb) possessed the NMR spectral characteristics of:

$^1$H NMR (400 MHz, CDCl$_3$): 9.59 (d, J=2.4 Hz, 1H), 0.52-2.58 (m, 21H)

Formula VI was described as having floral, muguet, green, aldehydic and fatty notes.

EXAMPLE VI

The fragrance properties of the above compounds were compared using (i) odor strength of 0 to 10, where 0=none, 1=very weak, 5=moderate, 10=extremely strong; and (ii) level of complexity, where 0=none, 1=very low, 5=moderate, 10=extremely high. Averaged scores are reported in the following:

| Compound | Odor Profile | Strength | Complexity |
|---|---|---|---|
| Formula I | Diffusive green top note with cucumber- and melon-like quality, perceived as natural. Floral, woody, muguet, aldehydic and orris-like. | 8 | 8 |
| Formula II | Green, fresh, melon-like, floral, ozonic and aldehydic with spicy cumin-like quality. | 9 | 9 |
| Formula VI | Floral, muguet, green, aldehydic but fatty. | 4 | 6 |
| Octahydro-4,7-methano-1H-indene-carboxaldehyde (Commercially available at IFF) | Green, fresh, melon-like, floral and ozonic with a solventy and kerosene-like quality. | 7 | 7 |

Formula I and Formula II each exhibited particularly desirable, strong, and complex odors, superior to the odors of close analogs such as Formula VI or octahydro-4,7-methano-1H-indenecarboxaidehycle. There is no structure-activity relationship observed and whether a given 4,7-methano-indene derivative possesses useful fragrance properties is therefore unpredictable. The advantageous fragrance properties of Formula I and Formula II are surprising and unexpected.

EXAMPLE VII

It was further found unexpectedly that Formula I is particularly suitable to be used in combination with a complementary fragrance compound. Such combinations are exemplified in the following:

| Complementary Fragrance Compound | Decanal | Methyl 3-oxo-2-pentylcyclopentaneacetate | 2-Tert-butyl-cyclohexyl acetate | 1-(2,6,6-Trimethyl-3-cyclohexen-1-yl)-2-buten-1-one | 1-(1,2,3,4,5,6,7,8,8A-Octahydro-2,3,8,8-tetramethyl-2-naphthalenyl)-ethan-1-one |
|---|---|---|---|---|---|
| Formula I | Fresh, juicy, aldehydic and citrusy with enhanced floral | Top note became greener and fuller bodied. A floral property emerged. | Fresh, fruity and green. The note was fuller bodied. The odor strength and | Sweet, floral and ozonic. Top note became fresher and greener. The odor | Woody and fruity with enhanced floral property. The note became greener and |

| Complementary Fragrance Compound | Decanal | Methyl 3-oxo-2-pentylcyclopentaneacetate | 2-Tert-butyl-cyclohexyl acetate | 1-(2,6,6-Trimethyl-3-cyclohexen-1-yl)-2-buten-1-one | 1-(1,2,3,4,5,6,7,8,8A-Octahydro-2,3,8,8-tetramethyl-2-naphthalenyl)-ethan-1-one |
|---|---|---|---|---|---|
| | property. The odor strength and dimension increased. | The odor strength increased. | dimension increased. | strength and dimension increased. | fuller bodied. The odor strength increased significantly. |
| Strength | 8 | 8 | 7 | 7 | 9 |
| Complexity | 6 | 8 | 8 | 7 | 8 |
| Octahydro-4,7-methano-1H-idenecarboxaldehyde | Aldehydic and citrusy with no noticeable changes. | Fresh with a slightly medicinal property. A camphoraceous note developed, which combined with a menthol-like odor, was perceived unpleasant. | Fresh, fruity, green with ozonic and melon-like top notes. Perceived thin bodied and synthetic. The combination appeared intrusive. | Fruity and green but solventy. Appeared synthetic and not desirable. | Woody, green, sweet and camphoraceous with an animalic property, perceived unpleasant. The combination appeared harsh and medicinal. |
| Strength | 2 | 4 | 5 | 4 | 4 |
| Complexity | 2 | 4 | 5 | 6 | 7 |

As shown, when compared with octahydro-4,7-methano-ifi-indenecarboxaidehyde. Formula I in the above combinations was particularly compatible and these combinations possessed desirable, strong and complex odors. Such advantageous properties are unexpected.

EXAMPLE VIII

It was further found unexpectedly that Formula II is particularly suitable to be used in combination with a complementary fragrance compound. Such combinations are exemplified in the following:

| Complementary Fragrance Compound | Decanal | Methyl 3-oxo-2-pentylcyclopentaneacetate | 2-Tert-butyl-cyclohexyl acetate | 1-(2,6,6-Trimethyl-3-cyclohexen-1-yl)-2-buten-1-one | 1-(1,2,3,4,5,6,7,8,8A-Octahydro-2,3,8,8-tetramethyl-2-naphthalenyl)ethan-1-one |
|---|---|---|---|---|---|
| Formula II | Aldehydic, juicy, fruity, citrusy with sweet and slightly floral top notes. The typical synthetic aspect of decanal reduced. | Sweet, muguet and aldehydic. The floral note strengthened and appeared more pleasant. Perceived being more dimensional and more complex. | Fresh, fruity and green with a warm top note. Appeared less synthetic. Perceived as being more dimensional and more complex. | Fresh, fruity, floral and green. The floral and woody notes strengthened and a honey note developed. Perceived as being more natural. | Soft, floral, sensual and natural. The buttery property enhanced. The medicinal note reduced. |
| Strength | 10 | 9 | 10 | 9 | 9 |
| Complexity | 9 | 9 | 10 | 9 | 10 |
| Octahydro-4,7-methano-1H-idenecarboxaldehyde | Aldehydic and citrusy with no noticeable changes. | Fresh with a slightly medicinal property. A camphoraceous note developed, which combined with a menthol-like odor, was perceived unpleasant. | Fresh, fruity, green with ozonic and melon-like top notes. Perceived thin bodied and synthetic. The combination appeared intrusive. | Fruity and green but solventy. Appeared synthetic and not desirable. | Woody, green, sweet and camphoraceous with an animalic property, perceived unpleasant. The combination appeared harsh and medicinal. |
| Strength | 2 | 4 | 5 | 4 | 4 |
| Complexity | 2 | 4 | 5 | 6 | 7 |

As shown, when compared with octahydro-4,7-inet13a3xo-114-mdertecarboxaldehyde, Formula II in the above combinations was particularly compatible and these combinations possessed desirable, strong and complex odors. Such advantageous properties are unexpected.

EXAMPLE IX

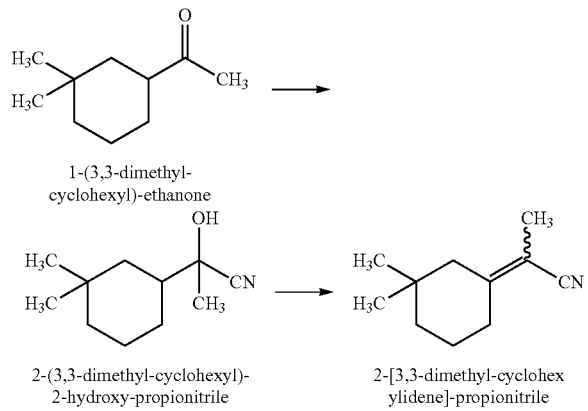

Preparation of 2-[3,3-Dimethyl-cyclohexylidene]-propionitrile (Formula V): 1-(3,3-dimethyl-cyclohexyl)-ethanone (700 g, 4.54 mol) was charged into a 5-L three neck flask equipped with a mechanic stirrer, an additional funnel and a thermometer followed by the addition of toluene (700 mL), water (300 mL) and potassium cyanide (KCN) (325 g, 4.99 mol). The mixture was stirred and acetic acid (410 g, 6.81 mol) was added dropwise while the temperature was kept under 35° C. with a water bath. The mixture was aged for additional 3 hours and the temperature was allowed to rise to room temperature. The resulting mixture was then poured into water and extracted with toluene. The organic layer was concentrated via a Rotavapor to provide the crude product 2-(3,3-dimethyl-cyclohexyl)-2-hydroxy-propionitrile (800 g, 4.41 mol). A solution of the crude product 2-(3,3-dimethyl-cyclohexyl)-2-hydroxy-propionitrile (658 g, 3.63 mol) in methylene chloride ($CH_2Cl_2$) (800 mL) and pyridine ($C_5H_5N$) (862 g, 10 mol) were then charged to a fresh 5-L three-necked flask equipped with a mechanic stirrer, an additional funnel and a thermometer. Thionyl chloride ($SOCl_2$) (475 g, 4 mol) was added to the stirred mixture dropwise while the temperature was kept to maintain a gentle reflux. The resulting mixture was aged for additional 5 hours at reflux and then then diluted with hexanes, cooled with an ice bath and filtered. The filtrate was subsequently concentrated and rushed over to provide the product 2-13,3-dimethyl-cyclohexylidenel-propionitrile (Formula V) (300 g).

2-[3,3-Dimethyl-cyclohexylidene]-propionitrile was described as having tobacco, hay, herbal, spicy, wood and fruity notes.

EXAMPLE X

Establishment of Malodor Models: The sweat, mold/mildew, bathroom and smoke malodor models were prepared based on Applicants' proprietary formulations for assessing the effectiveness of various malodor counteractants.

Preparation of Test Samples: Two aluminum dishes were placed in an 8 oz glass jar. A malodor material was pipetted into one aluminum dish, and a compound of the present invention (prepared as above in EXAMPLE I-IV and IX) diluted in a solvent (1%) or a solvent alone control was pipetted into the other aluminum dish. The jar was then capped and the samples were allowed to equilibrate for one hour before the testing.

Testing Procedure: Test samples were presented in a blind and random order to 15-18 internal panelists (consisting of men/women with an age range of 25 to 55). However, different odor samples were arranged in an alternative order (for example, sweat, mold/mildew, sweat, mold/mildew, and etc.).

The panelists were instructed to take the steps of i) sniff jars containing only the malodor materials for familiarization prior to the testing; ii) uncap a jar; iii) place their noses at a distance of about 3-4 inches above the opening; iv) take short sniffs for 3 seconds; and v) enter a rating of overall intensity and malodor intensity on a handheld computer.

The overall and malodor intensity was rated using the Labeled Magnitude Scale (LMS) [Green, et al., Chemical Senses, 21(3), Jun 1996, 323-334]. Percent malodor reduction ("% MOR") represents the perceived reduction in mean malodor intensity of the sample containing the malodor in the presence of a malodor counteractant relative to the negative control (Malodor Alone).

Results and Discussion: The mean ranks of the malodor coverage for the above test were as follows:

| Compound (1%) | Malodor | % MOR |
|---|---|---|
| Formula I | Sweat | 80.87 |
| | Mold/Mildew | 73.06 |
| | Bathroom | 79.88 |
| | Smoke | 72.24 |
| Formula II | Sweat | 59.63 |
| | Mold/Mildew | 58.63 |
| | Bathroom | 66.16 |
| | Smoke | 59.63 |
| Formula IV | Sweat | 50.32 |
| | Mold/Mildew | 48.43 |
| | Bathroom | 53.21 |
| | Smoke | 46.98 |
| Formula V | Sweat | 45.10 |
| | Mold/Mildew | 54.60 |
| | Bathroom | 76.04 |
| | Smoke | 45.10 |

Compounds of the present invention were demonstrated effective in counteracting various types of malodors.

What is claimed is:

1. A fragrance formulation comprising a fragrance compound selected from the group consisting of:
   (3aS,7aR)-3-(octahydro-4,7-methano-inden-1-yl)-propenal (rel);
   (3aS,7aR)-3-(octahydro-4,7-methano-inden-2-yl)-propenal (rel);
   a mixture of (3aS,7aR)-3-(octahydro-4,7-methano-inden-1-yl)-propenal (rel) and (3aS,7aR)-3-(octahydro-4,7-methano-inden-2-yl)-propenal (rel);
   (3aS,7aR)-3-(octahydro-4,7-methano-inden-1-yl)-propionaldehyde (rel);
   (3aS,7aR)-3-(octahydro-4,7-methano-inden-2-yl)-propionaldehyde (rel);
   a mixture of (3aS,7aR)-3-(octahydro-4,7-methano-inden-1-yl)-propionaldehyde (rel) and (3aS,7aR)-3-(octahydro-4,7-methano-inden-2-yl)-propionaldehyde (rel);
   (3aS,7aR)-3-[octahydro-4,7-methano-inden-(1E)-ylidene]-propionaldehyde (rel);
   (3aS,7aR)-3-[octahydro-4,7-methano-inden-(2E)-ylidene]-propionaldehyde (rel);
   a mixture of (3aS,7aR)-3-[octahydro-4,7-methano-inden-(1E)-ylidene]-propionaldehyde (rel) and (3aS,7aR)-3-[octahydro-4,7-methano-inden-(2E)-ylidene]-propionaldehyde (rel);

(3aS,7aR)-3-(3a,4,5,6,7,7a-hexahydro-3H-4,7-methano-inden-1-yl)-propionaldehyde (rel);
(3aR,7aS)-3-(3a,4,5,6,7,7a-hexahydro-1H-4,7-methano-inden-2-yl)-propionaldehyde (rel);
a mixture of (3aS,7aR)-3-(3a,4,5,6,7,7a-hexahydro-3H-4,7-methano-inden-1-yl)-propionaldehyde (rel) and (3aR,7aS)-3-(3a,4,5,6,7,7a-hexahydro-1H-4,7-methano-inden-2-yl)-propionaldehyde (rel); and
a mixture thereof.

2. The fragrance formulation of claim 1 further comprising a complementary fragrance compound.

3. The fragrance formulation of claim 1, wherein the fragrance compound is present in an amount from about 0.005 to about 50 weight percent of the fragrance formulation.

4. The fragrance formulation of claim 1, wherein the fragrance compound is present in an amount from about 0.5 to about 25 weight percent of the fragrance formulation.

5. The fragrance formulation of claim 1, wherein the olfactory acceptable fragrance compound is present in an amount from about 1 to about 10 weight percent of the fragrance formulation.

6. The fragrance formulation of claim 1 further comprising a material selected from the group consisting of a polymer, an oligomer and a non-polymer.

7. The fragrance formulation of claim 6, wherein the non-polymer is selected from the group consisting of a surfactant, an emulsifier, a fat, a wax, a phospholipid, an organic oil, a mineral oil, a petrolatum, a natural oil, a perfume fixative, a fiber, a starch, a sugar and a solid surface material.

8. The fragrance formulation of claim 7, wherein the solid surface material is selected from the group consisting of zeolite and silica.

9. A method of improving, enhancing or modifying a fragrance formulation through the addition of an olfactory acceptable amount of a compound selected from the group consisting of:
(3aS,7aR)-3-(octahydro-4,7-methano-inden-1-yl)-propenal (rel);
(3aS,7aR)-3-(octahydro-4,7-methano-inden-2-yl)-propenal (rel);
a mixture of (3aS,7aR)-3-(octahydro-4,7-methano-inden-1-yl)-propenal (rel) and
(3aS,7aR)-3-(octahydro-4,7-methano-inden-2-yl)-propenal (rel);
(3aS,7aR)-3-(octahydro-4,7-methano-inden-1-yl)-propionaldehyde (rel);
(3aS,7aR)-3-(octahydro-4,7-methano-inden-2-yl)-propionaldehyde (rel);
a mixture of (3aS,7aR)-3-(octahydro-4,7-methano-inden-1-yl)-propionaldehyde (rel) and (3aS,7aR)-3-(octahydro-4,7-methano-inden-2-yl)-propionaldehyde (rel);
(3aS,7aR)-3-[octahydro-4,7-methano-inden-(1E)-ylidene]-propionaldehyde (rel);
(3aS,7aR)-3-[octahydro-4,7-methano-inden-(2E)-ylidene]-propionaldehyde (rel);
a mixture of (3aS,7aR)-3-[octahydro-4,7-methano-inden-(1E)-ylidene]-propionaldehyde (rel) and (3aS,7aR)-3-[octahydro-4,7-methano-inden-(2E)-ylidene]-propionaldehyde (rel);
(3aS,7aR)-3-(3a,4,5,6,7,7a-hexahydro-3H-4,7-methano-inden-1-yl)-propionaldehyde (rel);
(3aR,7aS)-3-(3a,4,5,6,7,7a-hexahydro-1H-4,7-methano-inden-2-yl)-propionaldehyde (rel);
a mixture of (3aS,7aR)-3-(3a,4,5,6,7,7a-hexahydro-3H-4,7-methano-inden-1-yl)-propionaldehyde (rel) and (3aR,7aS)-3-(3a,4,5,6,7,7a-hexahydro-1H-4,7-methano-inden-2-yl)-propionaldehyde (rel); and
a mixture thereof.

10. The method of claim 9, wherein the fragrance formulation further comprising a complementary fragrance compound.

11. The method of claim 9, wherein the olfactory acceptable amount is from about 0.005 to about 50 weight percent of the fragrance formulation.

12. The method of claim 9, wherein the olfactory acceptable amount is from about 0.5 to about 25 weight percent of the fragrance formulation.

13. The method of claim 9, wherein the olfactory acceptable amount is from about 1 to about 10 weight percent of the fragrance formulation.

14. A fragrance product containing an olfactory acceptable amount of a fragrance compound selected from the group consisting of:
(3aS,7aR)-3-(octahydro-4,7-methano-inden-1-yl)-propenal (rel);
(3aS,7aR)-3-(octahydro-4,7-methano-inden-2-yl)-propenal (rel);
a mixture of (3aS,7aR)-3-(octahydro-4,7-methano-inden-1-yl)-propenal (rel) and
(3aS,7aR)-3-(octahydro-4,7-methano-inden-2-yl)-propenal (rel);
(3aS,7aR)-3-(octahydro-4,7-methano-inden-1-yl)-propionaldehyde (rel);
(3aS,7aR)-3-(octahydro-4,7-methano-inden-2-yl)-propionaldehyde (rel);
a mixture of (3aS,7aR)-3-(octahydro-4,7-methano-inden-1-yl)-propionaldehyde (rel) and (3aS,7aR)-3-(octahydro-4,7-methano-inden-2-yl)-propionaldehyde (rel);
(3aS,7aR)-3-[octahydro-4,7-methano-inden-(1E)-ylidene]-propionaldehyde (rel);
(3aS,7aR)-3-[octahydro-4,7-methano-inden-(2E)-ylidene]-propionaldehyde (rel);
a mixture of (3aS,7aR)-3-[octahydro-4,7-methano-inden-(1E)-ylidene]-propionaldehyde (rel) and (3aS,7aR)-3-[octahydro-4,7-methano-inden-(2E)-ylidene]-propionaldehyde (rel);
(3aS,7aR)-3-(3a,4,5,6,7,7a-hexahydro-3H-4,7-methano-inden-1-yl)-propionaldehyde (rel);
(3aR,7aS)-3-(3a,4,5,6,7,7a-hexahydro-1H-4,7-methano-inden-2 yl)-propionaldehyde (rel);
a mixture of (3aS,7aR)-3-(3a,4,5,6,7,7a-hexahydro-3H-4,7-methano-inden-1-yl)-propionaldehyde (rel) and (3aR,7aS)-3-(3a,4,5,6,7,7a-hexahydro-1H-4,7-methano-inden-2-yl)-propionaldehyde (rel); and
a mixture thereof.

15. The fragrance product of claim 14 further comprising a complementary fragrance compound.

16. The fragrance product of claim 14, wherein the fragrance product is selected from the group consisting of a perfume, a cologne, toilet water, a cosmetic product, a personal care product, a fabric care product, a cleaning product and an air freshener, a bar soap, a liquid soap, a shower gel, a foam bath, a cosmetic, a skin care product, a hair care product, a deodorant, an antiperspirant, a feminine care product, a baby care product, a family care product, a fabric product, an air care product, a fragrance delivery system, a cosmetic preparation, a cleaning agent, a disinfectant, a washing agent, a dental and oral hygiene product, a health care and nutritional product and a food product.

17. The fragrance product of claim 16, wherein the cleaning product is selected from the group consisting of a detergent, a dishwashing material, a scrubbing composition, a glass cleaner, a metal cleaner, a countertop cleaner, a floor cleaner, a carpet cleaner, a toilet cleaner and a bleach additive.

18. The fragrance product of claim 16, wherein the washing agent is selected from the group consisting of a laundry detergent and a rinse additive.

\* \* \* \* \*